(12) United States Patent
Murthy

(10) Patent No.: US 12,065,632 B2
(45) Date of Patent: Aug. 20, 2024

(54) CELL CULTURE CHAMBERS AND METHODS OF USE THEREOF

(71) Applicant: Northeastern University, Boston, MA (US)

(72) Inventor: Shashi K. Murthy, Newton, MA (US)

(73) Assignee: Northeastern University, Boston, MA (US)

( * ) Notice: Subject to any disclaimer, the term of this patent is extended or adjusted under 35 U.S.C. 154(b) by 231 days.

(21) Appl. No.: 16/310,680

(22) PCT Filed: Jun. 27, 2017

(86) PCT No.: PCT/US2017/039538
§ 371 (c)(1),
(2) Date: Dec. 17, 2018

(87) PCT Pub. No.: WO2018/005521
PCT Pub. Date: Jan. 4, 2018

(65) Prior Publication Data
US 2020/0308523 A1  Oct. 1, 2020

Related U.S. Application Data

(60) Provisional application No. 62/356,504, filed on Jun. 29, 2016, provisional application No. 62/357,937, filed on Jul. 1, 2016.

(51) Int. Cl.
*C12M 3/00* (2006.01)
*C12M 1/00* (2006.01)
(Continued)

(52) U.S. Cl.
CPC ............ *C12M 23/58* (2013.01); *C12M 23/20* (2013.01); *C12M 23/24* (2013.01); *C12M 29/14* (2013.01);
(Continued)

(58) Field of Classification Search
CPC .............................. C12M 23/24; C12M 23/20
See application file for complete search history.

(56) References Cited

U.S. PATENT DOCUMENTS 4,201,845 A * 5/1980 Feder ..................... C12M 29/04
435/297.2
4,939,151 A * 7/1990 Bacehowski .......... C12M 23/08
206/484.1
(Continued)

FOREIGN PATENT DOCUMENTS

CN 101563464 A 10/2009
CN 102112594 A 6/2011
(Continued)

OTHER PUBLICATIONS

Transmittal of International Preliminary Report on Patentability in PCT/US2017/039538, titled: Cell Culture Chambers and Methods of Use Thereof, Date of Mailing: Jan. 10, 2019.
(Continued)

*Primary Examiner* — Nathan A Bowers
(74) *Attorney, Agent, or Firm* — Hamilton, Brook, Smith & Reynolds, P.C.

(57) ABSTRACT

The invention provides cell culture chambers and methods of use thereof. In certain embodiments, the cell culture chambers and methods provide for an expansion and stimulation of T-cells using autologous antigen-presented cells to provide a therapeutic T-cell product that can mobilize a patient's own immune system in a manner that selectively targets a patient's tumor.

16 Claims, 10 Drawing Sheets

(51) Int. Cl.
  *C12M 1/04* (2006.01)
  *C12M 1/26* (2006.01)
  *C12M 1/36* (2006.01)
  *C12M 1/42* (2006.01)

(52) U.S. Cl.
  CPC ............ *C12M 33/12* (2013.01); *C12M 35/08* (2013.01); *C12M 41/48* (2013.01); *C12M 47/10* (2013.01)

(56) References Cited

U.S. PATENT DOCUMENTS

| | | | | |
|---|---|---|---|---|
| 5,536,662 | A | * | 7/1996 | Humphries ............ C12M 25/04 204/403.02 |
| 5,763,266 | A | | 6/1998 | Palsson et al. |
| 6,607,910 | B1 | * | 8/2003 | Dimitrijevich ........ C12M 23/06 435/297.1 |
| 2002/0110905 | A1 | | 8/2002 | Barbera-Guillem et al. |
| 2005/0014129 | A1 | * | 1/2005 | Cliffel ................ G01N 33/5038 435/4 |
| 2008/0227176 | A1 | * | 9/2008 | Wilson ................... C12M 23/08 435/243 |
| 2013/0224736 | A1 | * | 8/2013 | Marie ............... B01L 3/502761 435/6.1 |
| 2014/0004557 | A1 | * | 1/2014 | Ma ....................... B01L 3/5027 435/283.1 |

FOREIGN PATENT DOCUMENTS

| | | |
|---|---|---|
| CN | 204803326 U | 11/2015 |
| EP | 2 623 587 A1 | 8/2013 |
| JP | 60-3474 | 1/1985 |
| JP | 2006122012 A | 5/2006 |
| JP | 2010220605 A | 10/2010 |
| JP | 2010252631 A | 11/2010 |
| WO | 03014291 A1 | 2/2003 |
| WO | 2005/113742 A1 | 12/2005 |
| WO | 2009/104296 A1 | 8/2009 |
| WO | 2012/147463 A1 | 11/2012 |
| WO | 2013/145235 A1 | 10/2013 |
| WO | 2017/004169 A1 | 1/2017 |

OTHER PUBLICATIONS

International Search Report and Written Opinion dated Feb. 5, 2018 for International Application No. PCT/US2017/039538 entitled, "Cell Culture Chambers and Methods of Use Thereof".

Robbins PF, et al., "Mining exomic sequencing data to identify mutated antigens recognized by adoptively transferred tumor-reactive T cells;" Nat Med. 2013;19(6):747-52.

Tran E, et al., "Immunogenicity of somatic mutations in human gastrointestinal cancers;" Science. 2015;350(6266):1387-90.

Tran E, et al., "Cancer Immunotherapy Based on Mutation-Specific CD4+T Cells in a Patient with Epithelial Cancer;" Science. 2014;344(6184):641-5.

Vera JF, et al., "Accelerated Production of Antigen-specific T Cells for Preclinical and Clinical Applications Using Gas-permeable Rapid Expansion Cultureware (G-Rex);" J Immunother. 2010;33(3):305-15.

Janelle V., et al., "Defining novel parameters for the optimal priming and expansion of minor histocompatibility antigen-specific T cells in culture;" J. Transl. Med. 2015;13.

Zhang BY, et al., "A standalone perfusion platform for drug testing and target validation in micro-vessel networks;" Biomicrofluidics. 2013;7(4).

Green JV, et al., "Effect of channel geometry on cell adhesion in microfluidic devices;" Lab Chip. 2009; 9(5):677-85.

Kim S., et al., "Controlling duration of contact between T cells and antigen-presenting cells;" J. Immunol. Methods, 2001; 249(1-2):73-84.

Mirsky HP, et al., "Systems biology approaches for understanding cellular mechanisms of immunity in lymph nodes during infection;" J.Theor. Biol. 2011; 287:160-70.

Valitutti S, Coombs D, Dupre L. The space and time frames of T cell activation at the immunological synapse. FEBS Lett. 2010;584(24):4851-7.

Vroomans RMA, et al., "Chemotactic Migration of T Cells towards Dendritic Cells Promotes the Detection of Rare Antigens;" PLoS Comput. Biol. 2012; 8(11).

Beltman JB, et al., "Towards estimating the true duration of dendritic cell interactions with T cells;" J. Immunol. Methods. 2009; 347(1-2):54-69.

Day M., et al., "Timescales of the Adaptive Immune Response;" In: Mathematical Models and Immune Cell Biology. Molia-Paris C, Lythe G, editors, Springer; 2011.

Vickers Dal, et al., "Lectin-functionalized microchannels for characterizing pluripotent cells and early differentiation;" Biomicrofluidics. 2012; 6(2):024122.

Brandrup J., et al., Polymer Handbook. Second Edition; New York: Wiley; 1975.

* cited by examiner

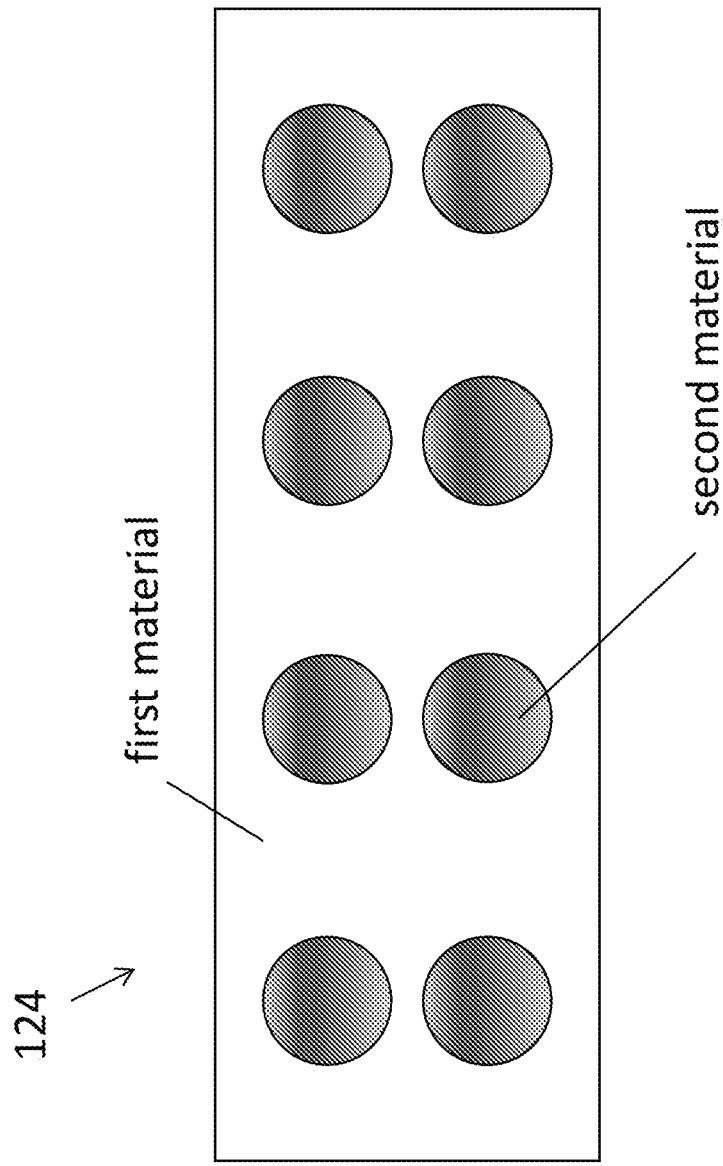

CELL CULTURE CHAMBERS AND METHODS OF USE THEREOF

CROSS REFERENCE TO RELATED APPLICATIONS

This application claims the benefit of and priority to U.S. Provisional Application No. 62/356,504, filed Jun. 29, 2016, and U.S. Provisional Application No. 62/357,937, filed Jul. 1, 2016, both of which are incorporated herein by reference in their entirety.

GOVERNMENT SUPPORT

This application is the U.S. National Stage of International Application No. PCT/US2017/039538, filed Jun. 27, 2017, which designates the U.S., published in English, and claims the benefit of and priority to U.S. Provisional Application No. 62/356,504, filed Jun. 29, 2016, and U.S. Provisional Application No. 62/357,937, filed Jul. 1, 2016. The entire teachings of the above applications are incorporated herein by reference.

FIELD OF THE INVENTION

The invention generally relates to cell culture chambers and methods of use thereof.

BACKGROUND

Cell-based cancer immunotherapy has received a lot of attention based on extraordinary promising treatments for certain cancers based on chimeric antigen receptor T cell (CAR-T) therapy, T cell receptor (TCR) therapy, dendritic cell vaccines, and neoantigen-based T cell therapy. In the latter therapy, the ability to predict candidate neoantigens from tumor sequencing data and the monitoring of neoantigenic-specific T-cell responses in patients provides a basis for designing highly personalized immunotherapeutics.

While T-cell therapy for cancer holds great promise, existing processes for isolation, preparation, and expansion of cancer antigen-specific T-cells are limited. Currently, T-cell therapies are prepared using labor-intensive, manual, multi-step processes, which pose serious challenges for scaling in manufacturing such T-cell therapies. Automating this process has been unsuccessful due to the complex biological processes associated with T-cell therapy production as well as the bioprocess and regulatory requirements associated with autologous cell processing. Additional challenges also exist, such as time of cell preparation, maintenance of optimal phenotype, expansion to sufficient cell number, and quality and safety of the cell product.

As shown in FIG. 1, the conventional prior art protocol for stimulation of human T cells by autologous antigen-presenting dendritic cells (DCs) involves several manual steps, including the transfer of supernatant between culture plates, the change of media, addition of cytokines and cell medium, etc. T-cells are placed in contact with dendritic cells (DCs) for seven days, during which time they become stimulated and expand. This process is typically repeated four times, with each stimulation cycle requiring extraction of the T-cells in the supernatant and plating with fresh DCs, while also manually exchanging medium and growth factors (cytokines), typically twice during each seven day period. The number of manual steps required to carry out the protocol is prohibitively high. For example, using this conventional four week protocol, a total of approximately 4,650 manual steps are taken, all of which add to the risk of contamination and can compromise the quality and safety of the cell product.

SUMMARY

The invention recognizes that there exists a need to develop new technology that automates the production of antigen-specific T-cells. The cell culture chambers of an example embodiment of the invention include various technical features that allow for the automation of the above described manual process, dramatically reducing user intervention in the process and thereby significantly reducing the risk of contamination. For example, cell culture chambers of the embodiment are fabricated to include a bottom surface that is made of a material to which cells adhere and at least one additional surface, such as the side walls and/or the top wall, that is made of a gas permeable material. In this way, greater levels of gas exchange are achieved without having to sacrifice the adherent nature of the bottom surface, as compared to prior art culture systems. Additionally, cell culture chambers of the embodiment are configured to allow for culture medium and cytokines to be perfused into the chamber such that more consistent levels can be maintained. In order to ensure that the antigen-specific T-cells and other cells involved in the culturing process remain in the chamber during perfusion, one or more inlets and outlets of the cell culture chamber are arranged to move fluid within the cell culture chamber at least in part along a vertical flow path upon exiting the chamber. Cell culture chambers are also configured to fluidically connect to one another, such that antigen-specific T-cells can be automatically transferred between chambers to allow for further culturing and expansion of the T-cells in a new cell culture chamber. In some embodiments, transfer is effectuated by introducing a gas flow into the first cell culture chamber to transfer a supernatant including the first cell product through a fluidic connector and into a second cell culture chamber.

In certain aspects, the cell culture chambers of the example embodiment provide for the expansion and stimulation of T-cells using antigen-presented cells from the same patient to provide a therapeutic T-cell product that can mobilize a patient's own immune system in a manner that selectively targets a patient's tumor. These cell culture systems and methods greatly reduce the number of manual steps compared to conventional protocols. In this way, the risks of contamination are greatly decreased and the robustness and reproducibility of the manufacturing technique are greatly increased, both key considerations for safe and reliable manufacturing of therapeutic products, such as personalized T cell therapies capable of precise targeting.

Beyond simplifying and potentially shortening the process of generating immunotherapeutic products, the cell culture chambers of the example embodiment significantly improve the utilization of a patient's cellular material for cell-based therapies and the reliability and robustness of the manufacturing process, while also leading to cost reductions (e.g., labor costs). Furthermore, methods are readily scalable from the processing of only a few patient samples to 100s of patient samples. The configuration of the cell culture chambers of the embodiment allows for automated fluid flow control to bring antigen-presenting cells into contact with T-cell containing cells, as well as to refresh the antigen-presenting cells as necessary, in order to stimulate and expand the antigen presenting T-cells to a number that is capable of producing a therapeutic response in a patient. This design is also easily scalable. For example, by designing a system with a series of cell culture chambers arranged in parallel, a single system can process samples ranging from 1-10 to 100s of samples. Each chamber can be independently controlled, and the number of chambers utilized at any given time can be scaled up or down depending on the number of samples. In other embodiments, a single central controller, such as a PLC logic controller, controls all of the chambers in the system.

An example arrangement is now described in which systems and methods of an example embodiment of the invention utilize one or more bioreactors, each comprising a cell culture chamber, that are configured to be fluidically coupled to one another for carrying out the processing of a patient's cellular material to generate an immunotherapeutic product. The skilled artisan will appreciate that this is an example arrangement described herein and that other arrangements are within the scope of the invention.

In this example embodiment, a cell culture chamber is provided that includes a bottom surface comprising a first material to which cells adhere, at least one additional surface, wherein the least one additional surface comprising a second material that is gas permeable, one or more inlets, and one or more outlets, wherein the one or more inlets and the one or more outlets are arranged to move fluid within the cell culture chamber at least in part along a vertical flow path. In certain aspects, movement of the fluid along the vertical flow path is such that a fluid flow rate is insufficient to overcome a settling rate of cells within the cell culture chamber.

The provision of at least one additional gas permeable surface that allows for a greater level of gas exchange compared to conventional protocol, thus allowing for greater numbers of cells to be processed in the chamber. In certain aspects, the bottom surface and at least one additional surface are joined together without using an adhesive. In certain embodiments, the at least one additional surface also comprises the first material.

The first material can comprise, for example, polystyrene. The second material can comprise one or more materials having permeability to oxygen at or greater than permeability coefficient of 350 and permeability to carbon dioxide at or greater than permeability coefficient of 2000, where the unit of permeability coefficient is $[cm^3][cm]/[cm^2][s][cm\ Hg]$. In one aspect, the second material is selected from one or both of silicone and polymethylpentene.

In certain aspects, the cell culture chamber includes at least one fluidic connector configured to fluidically couple the cell culture chamber to a second vessel, which can be a second cell culture chamber. To assist with the flow of fluid through each chamber and between chambers, the cell culture chamber can comprise one or more pumps. Each chamber can comprise its own pump of one or more pumps can service multiple chambers. In other aspects, the cell culture chamber further includes one or more fluid reservoirs that are operably coupled to the one or more pumps. The fluid reservoirs are configured to supply medium, which includes nutrients and cytokines, to the chamber.

The cell culture chamber can also include one or more sensors operably coupled to the cell culture chamber in a manner that allows the sensors to measure one or more parameters, such as pH, dissolved oxygen, total biomass, cell diameter, glucose concentration, lactate concentration, and cell metabolite concentration, within the cell culture chamber. The cell culture chamber may further comprise a central processing unit communicatively coupled to the one or more sensors and configured to adjust an operating state of the one or more pumps as a function of the one or more parameters measured. In an embodiment in which a flow generating mechanism is employed rather than pumps, such as an electrohydrodynamics mechanism, the central processing unit may change an operating state of the flow generating mechanism to adjust a rate of flow of the first cell product as a function of the one or more parameters.

In certain embodiments, in order to help maintain a desired environment in and around the cell culture chamber, the chamber is sized and configured to fit within an incubator. In some embodiments, the one or more pumps are located within the incubator. In other embodiments, the one or more pumps are located outside of the incubator and operably coupled to the cell culture chamber within the incubator.

In certain aspects, at least part of the system comprises disposable components, some or all of which can be housed within a non-disposable frame. In other aspects, all components of the system are disposable. Furthermore, in some embodiments, the system includes a sample tracking component for tracking and documenting patient material.

The systems and methods are designed such that any number of additional reactors, or cell culture chambers, can be provided. In some embodiments, the system includes two or more bioreactor chambers for generating T-cells, as shown in FIGS. 6A and 6B. Although the system in FIGS. 6A and 6B is shown as having two cell culture chambers in fluidic communication with each other, it is to be understood that any number of additional chambers can be used with the system.

In certain embodiments, systems of the invention have the capability to automatically calculate and set a desired perfusion rate of perfusion fluid given various inputs, such as the size of the cell culture chamber and the concentrations of two or more cell types including dendritic cells and peripheral blood mononuclear cells. In an example arrangement, a cell culture system is provided that includes one or more cell culture chambers and a central processing unit comprising memory containing instructions executable by the central processing unit to cause the system to receive as a first input data comprising a size of the cell culture chamber, receive as a second input data comprising a first concentration of a first cell type and a second concentration of a second cell type in one or more fluids that will be introduced into the cell culture chamber, and calculate, based on the first and second inputs, a perfusion rate of a perfusion fluid that will be introduced into the cell culture chamber that maximizes a probability of the first cell type and the second cell type contacting each other within the cell culture chamber. In certain aspects, the first cell type is a peripheral blood mononuclear cell and the second cell type is a dendritic cell.

The central processing unit can control the perfusion rate of the perfusion fluid by controlling one or more pumps (or valves) operably coupled to one or more perfusion fluid reservoirs and the central processing unit. In certain aspects, one or more sensors are operably coupled to the cell culture chamber in a manner that allows the sensors to measure one or more parameters within the cell culture chamber. These parameters include pH, dissolved oxygen, total biomass, cell diameter, glucose concentration, lactate concentration, and cell metabolite concentration.

In another aspect of the invention, a method for transferring cells from a first cell culture chamber into a second cell culture chamber is provided. The method generally includes culturing cells in a first cell culture chamber in a manner that generates a supernatant comprising a first cell product, and introducing a gas flow into the first cell culture chamber to transfer the supernatant comprising the first cell product through a fluidic connector and into a second cell culture chamber. Once the fluid enters the second cell culture chamber, the first cell product is further cultured.

Similar to the transfer of fluid from the first cell culture chamber to the second cell culture chamber, the method may also include introducing a gas flow into the second cell culture chamber to transfer the supernatant comprising the further cultured first cell product through a fluidic connector and into a third cell culture chamber. In one embodiment, the transfer of supernatant occurs at least three different times, such that at least four culture chambers are used to produce the desired quantity of antigen-presenting T-cells.

Furthermore, in certain aspects, as noted above, one or more of the cell culture chambers are configured to move fluid, such as perfusion fluid, through the chamber along a vertical flow path (FIG. 8C). The movement of the fluid is such that a fluid flow rate is insufficient to overcome a settling rate of cells within the cell culture chamber.

In yet another aspect of the invention, methods for generating an immunotherapeutic product include culturing peripheral blood mononuclear cell and dendritic cells in a first cell culture chamber to produce a supernatant comprising T-cells, and introducing a gas flow into the first cell culture chamber to transfer the supernatant comprising the T-cells through a fluidic connector and into a second cell culture chamber. In certain aspects, fresh dendritic cells are contained within the second cell culture chamber, and the T-cells are further cultured within the second cell culture chamber.

Culturing within the first culture chamber can occur in the presence of a first set of one or more stimulating antigens and culturing within the second culture chamber can occur in the presence of a second set of stimulating antigens. In certain embodiments, the first set of stimulating antigens and the second set of stimulating antigens are the same. While in other embodiments, the first set of stimulating antigens and the second set of stimulating antigens are different.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The patent or application file contains at least one drawing executed in color. Copies of this patent or patent application publication with color drawing(s) will be provided by the Office upon request and payment of the necessary fee.

FIG. 5 depicts a surface of a cell culture chamber having a configuration that incorporates a permeable polymer within a frame of another polymer.

FIG. 6A is the schematic of the first cell culture chamber as shown in FIG. 3. FIG. 6B illustrates the partially expanded T-cells in the first cell culture chamber and the movement of the second cell culture chamber into position for connection to the first cell culture chamber. FIG. 6C illustrates the injection of sterile air into the first cell culture chamber to transfer the supernatant containing the expanded T-cells into the second cell culture chamber.

FIGS. 8A and B depict a planar flow of fluid in and out of a cell culture chamber. FIGS. 8C and D depict a configuration with symmetric inflows and vertical outflows.

DETAILED DESCRIPTION

Devices, systems, and methods of the present invention make it possible to automate as well as to remotely monitor and control methods of generating sufficient quantities of antigen specific T-cells for personalized targeted cancer or infectious disease therapy that involve the culturing of autologous cells. The systems and methods of the invention include various technical features that allow for the automation of the above described manual process. These technical features include, but are not limited to, 1) the construction of the cell chambers to include a bottom surface that is made of a material to which cells adhere and at least one additional surface that is made of a gas permeable material, such that greater levels of gas exchange are achieved, 2) the arrangement of one or more inlets and outlets of the cell culture chamber to move fluid within the cell culture chamber along a vertical flow path upon exiting the chamber to ensure that the antigen-specific T-cells and other cells involved in the culturing process remain in the chamber during perfusion of culturing medium, and 3) the automatic transfer of antigen-specific T-cells from one chamber to another by introducing a gas flow into the first cell culture chamber to transfer the cells through a fluidic connector and into a second cell culture chamber.

The methods, devices, and systems of the invention can be scaled up to provide a large number of cell-based immunotherapeutic products, and can be operated either for a single subject or for several subjects in parallel (whereby their cells and the progeny thereof remain separate). Compared to prior art methods and devices, the methods and systems of the invention are robust in their operation, capable of providing high product yields, simple and efficient, involve less risk for contamination, and reduce the costs of labor to a minimum.

Figure 2:
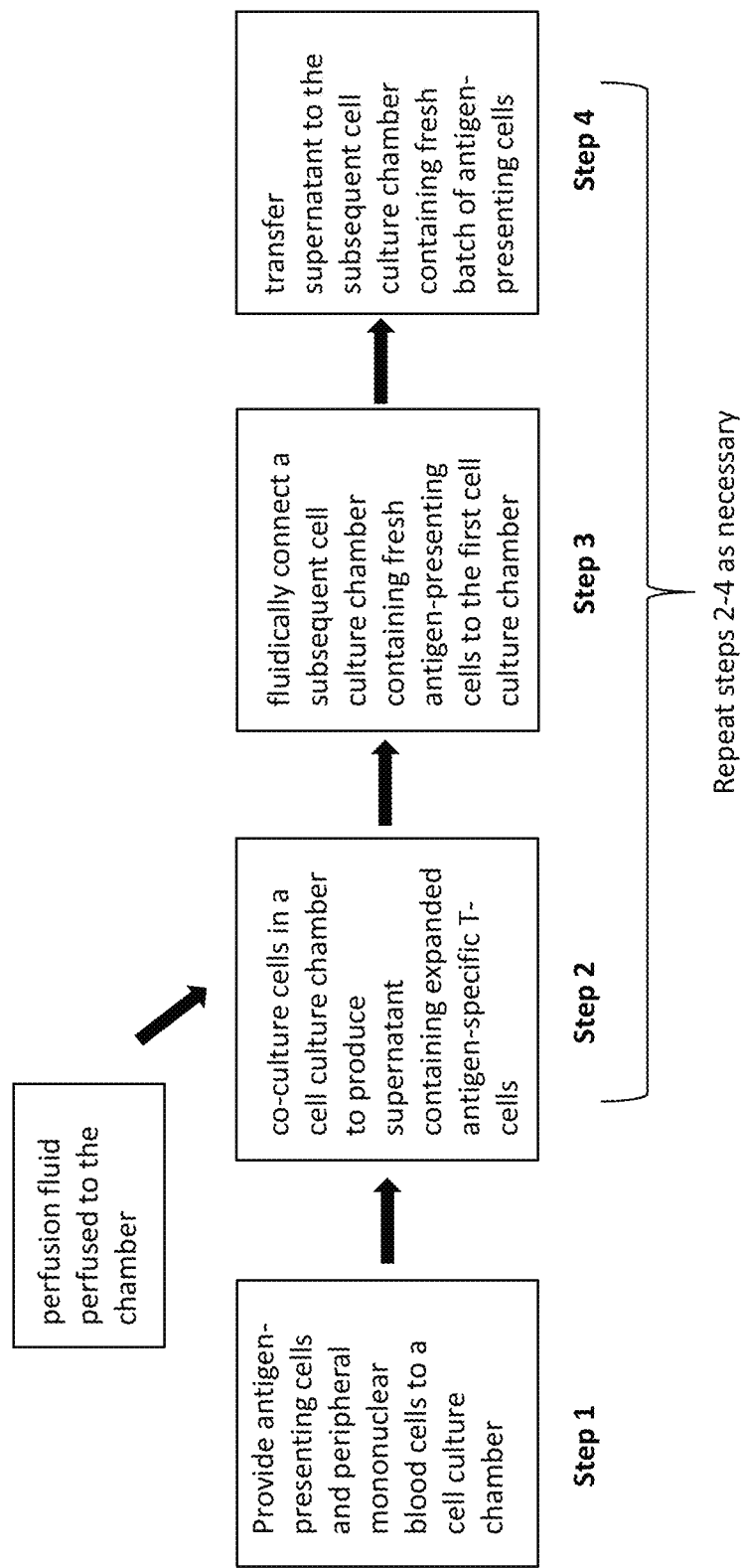
FIG. 2 shows an example method for producing immunotherapeutic products in accordance with an embodiment of the present invention.

FIG. 2 shows an overview of a method for generation of cell-based immunotherapeutic products using the systems described herein. Briefly, the steps in generating cellular therapeutic product in accordance with certain embodiments of the present invention include the co-culturing of stimulated antigen-presenting cells with T-cell containing cells in a biological reactor containing a cell culturing chamber. A supernatant containing expanded therapeutic T-cell products is generated during culturing. In certain aspects, in order to produce a quantity of antigen-specific T-cells sufficient to elicit a therapeutic response in a patient, the T-cells must undergo additional culturing in one or more additional cell culturing chambers. In order to effectuate this additional culturing, the transfer of supernatant from the culture chamber in which the supernatant was generated to a subsequent cell culture chamber containing a fresh supply of antigen-presenting cells must occur. The transfer of supernatant between cell culture chambers may involve the introduction of a gas flow into the first cell culture chamber that transfers the supernatant comprising the first cell product through a fluidic connector and into the new cell culture chamber. Furthermore, during each of the culturing steps, perfusion fluid containing, for example, medium and cytokines, can be perfused to the chambers. In certain aspects, the perfusion fluid flows through the chambers along a vertical flow path so as to ensure that the cells remain within the chamber during culturing. The only manual steps involved using the systems of the invention are the provision of one or more subsequent biological reactors to the system, each reactor containing a cell culture chamber, with each chamber containing a new batch of antigen peptide-pulsed autologous antigen-presenting cells.

Figure 1:
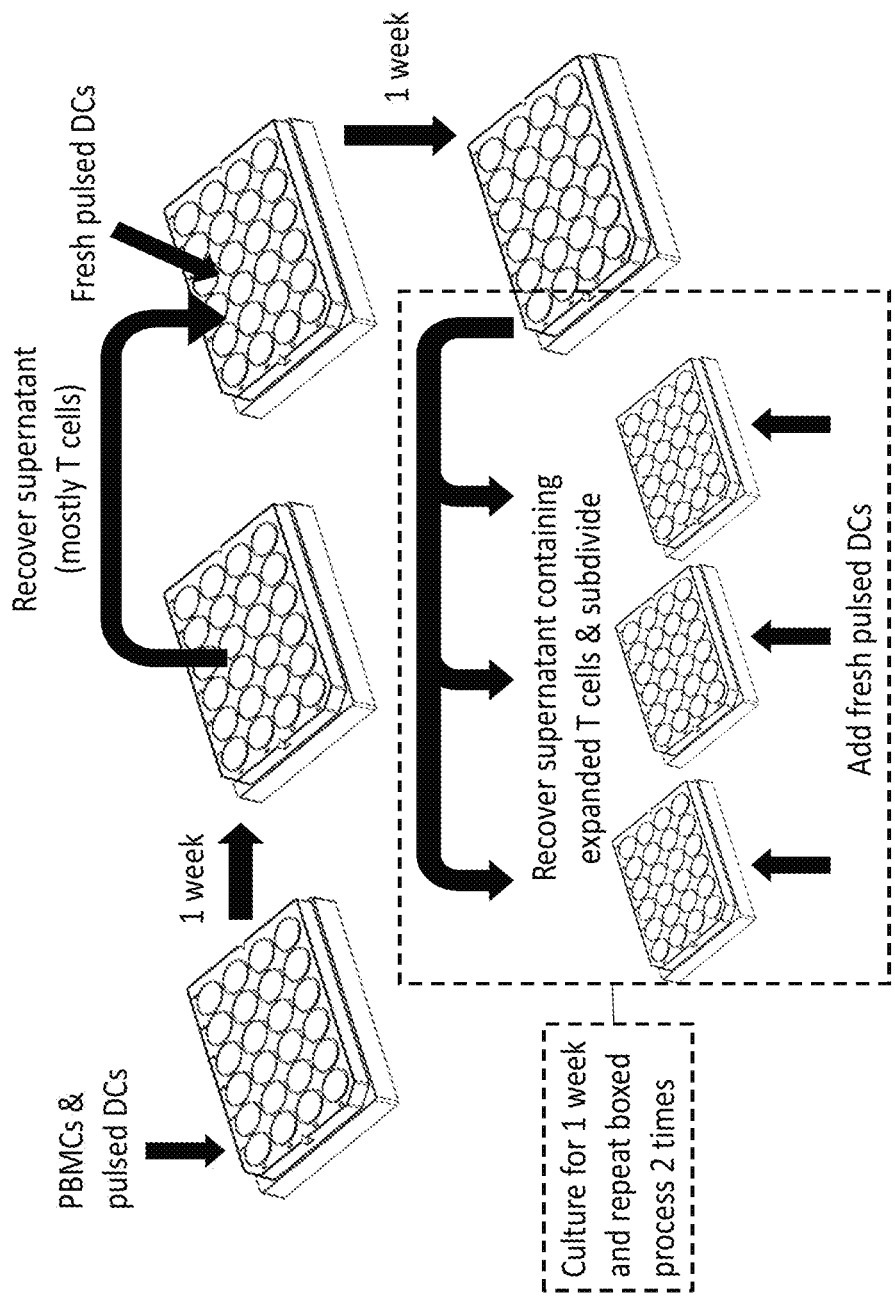
FIG. 1 shows a prior art manual technique for producing immunotherapeutic products.
Figure 3:
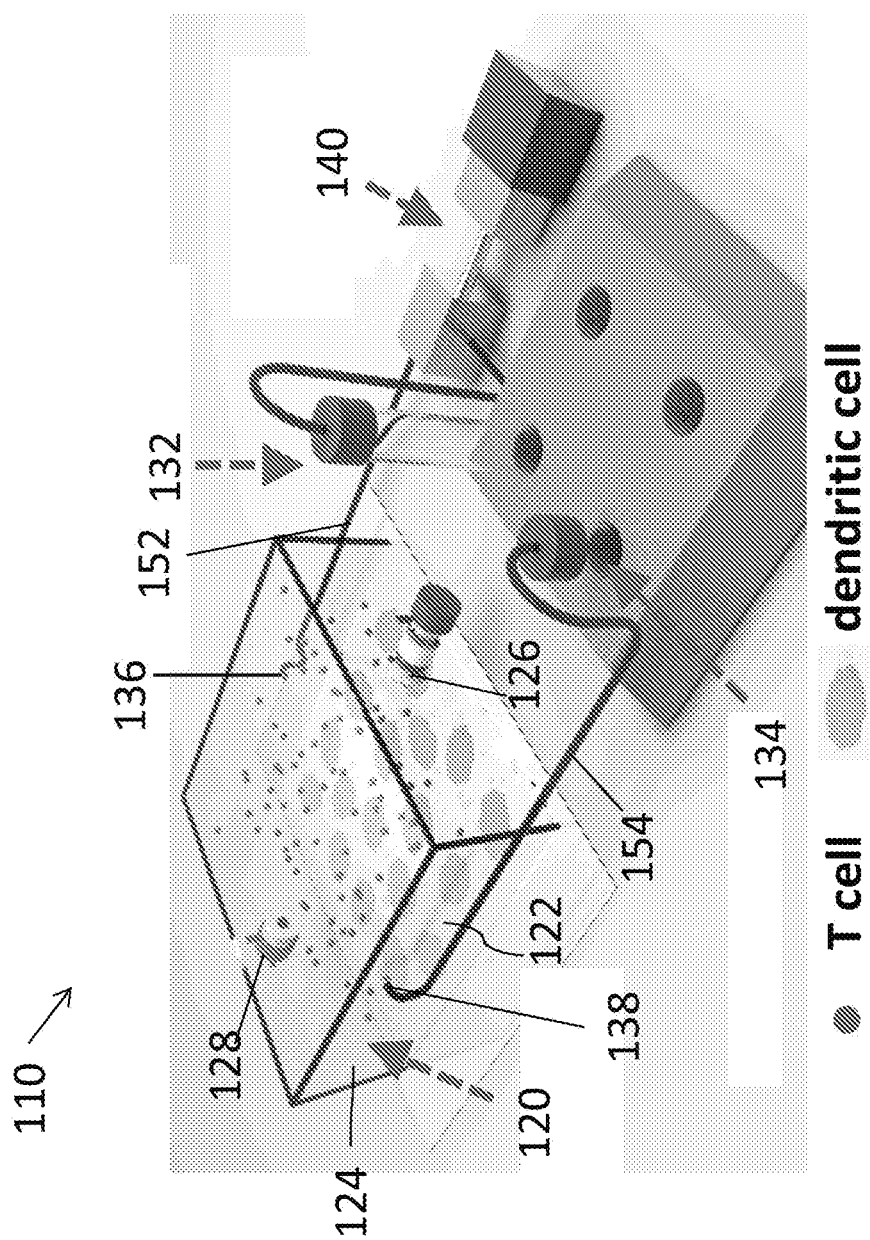
FIG. 3 is a schematic depicting a system of the invention in one embodiment, with one cell culture chamber shown.

The method of generating cell-based immunotherapeutic products according to embodiments of the present invention is far simpler and more efficient than methods of the prior art. FIG. 1 shows the prior art conventional protocol that requires at least 4,650 manual steps, as described previously. In contrast, the systems and methods of the present invention, as shown in FIGS. 2-4 and described herein, involve a 25 fold decrease in the number of manual steps that need to be taken to generate the same cell dose, as shown in Table 1 below.

comprised of a first material to which cells adhere, wherein the at least one additional surface 124 is comprised of a second material that is gas permeable. The cell culture chamber also comprises one or more inlets 126, 136 and one or more outlets 128, 138. In certain embodiments, the biological reactor also includes at least one perfusion fluid reservoir 132, at least one waste fluid reservoir 134, at least one pump 140 for moving perfusion fluid through the chamber 120, as well as associated inlets 136 and outlets 138 for transporting fluid to and from the reservoirs 132, 134 and through the chamber 120.

With respect to the cell culture chamber 120, the first material can be any material which is biocompatible and to which antigen-presenting cells (APCs), such as dendritic cells (DCs) will adhere. During the T-cell stimulation and expansion process that occurs in the cell culture chamber 120, mature APCs will develop and preferably adhere to the bottom surface 122, whereas the T-cells remain in the supernatant above the bottom surface, making it easier to separately obtain the expanded T-cells.

In one example embodiment, the first material comprises polystyrene. One benefit of using polystyrene for the bottom surface where culturing will occur is a useful role that this material plays in the process of generating dendritic cells from PBMCs. Specifically, polystyrene surfaces can be used to enrich monocytes from a heterogeneous suspension of PBMCs. This is a first step in the culture process utilized to generate DCs by differentiation of monocytes via culture in medium containing, for example, IL4 and GM-CSF. The use

TABLE 1

Typical Steps in Antigen-Specific T-Cell Generation

| Category | Conventional Protocol | Presently Disclosed Protocol |
| --- | --- | --- |
| Type of plate | 24-well | Cell culture chamber |
| Volume per well | 2 mL | 2-10 mL; multiplexing possible |
| No. of media changes | 4 per month | None; chambers are preloaded with medium |
| Additional of cytokines | 8 per month | None; chambers are preloaded with cytokines |
| Transfer to new plates | 3 (re-stimulations per month) | 3 (re-stimulations per month) |
| No. of plates | 310 plates for $10^{10}$ cell dose | 50-60 reactors for $10^{10}$ cell dose |
| Opening of incubators | ~36 times per month | ~4 times per month |
| Total Manual Steps | 4 + 8 + 3) × 310 = 4,650 | 60 × 3 = 180 |

The cell culture chambers of the present invention significantly improve immunotherapeutic product manufacturing, providing flow-based immunotherapeutic production technology with an unparalleled degree of consistency, quality, safety, economy, scalability, flexibility, and portability.

An example arrangement is now described in which systems and methods of the invention utilize one or more bioreactor, each reactor containing a cell culture chamber, configured to be fluidically coupled to one another for carrying out the processing of a patient's cellular material to generate an immunotherapeutic product. It is to be understood that the bioreactors are provided in a closed environment in certain embodiments. Scale-up of this example embodiment will be within the knowledge of the skilled artisan by adding modules (e.g., biological reactors) to allow for serial and/or parallel processing. The skilled artisan will also appreciate that different or alternative arrangements may be desired based on the product to be produced.

In an example embodiment, as shown in FIG. 3, a biological reactor 110 is provided including a cell culture chamber 120 that includes a bottom surface 122 and at least one additional surface 124. The bottom surface 122 is of the same polystyrene surface for dendritic cell production all the way through one cycle of T-cell stimulation is tremendously valuable from a bioprocess standpoint as it eliminates a large number of transfer steps that would otherwise be necessary, thereby allowing for a closed system for DC-stimulated therapeutic T-cell manufacturing.

The bottom surface can have a surface area comparable to conventional well plates, such as 6- and 24-well plates (9.5 cm$^2$ and 3.8 cm$^2$, respectively). It is also to be understood that the surface area can be smaller or even much larger than conventional well plates (e.g., having surface areas comparable to standard cell culture dishes and flasks), such as having a surface area between about 2.0 cm$^2$ and about 200 cm$^2$, for example, about 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 55.0, 60.0, 65.0, 70.0, 75.0, 100.0, 125.0, 150.0, 175.0, and 200.0 cm$^2$, and any surface area in between.

Figure 4C:
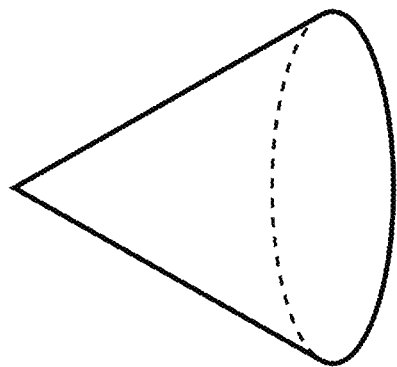
FIGS. 4A-E depict example cell culture chamber configurations in accordance with embodiments of the present invention.
Figure 4B:
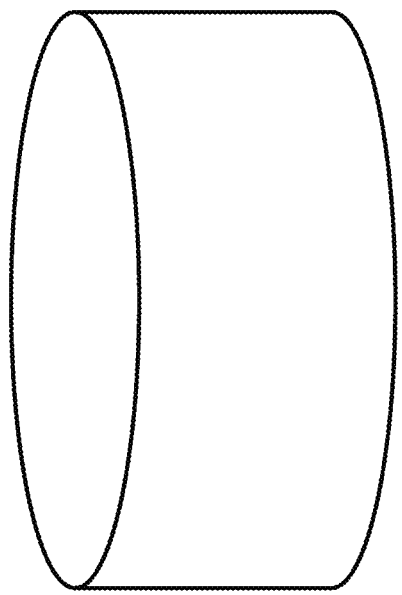
Figure 4A:
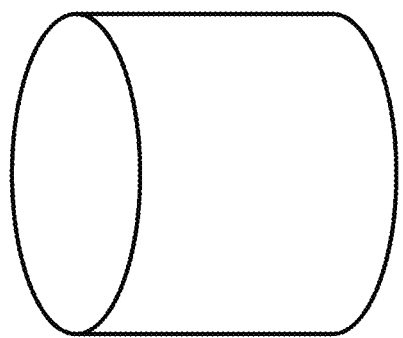
Figure 4E:
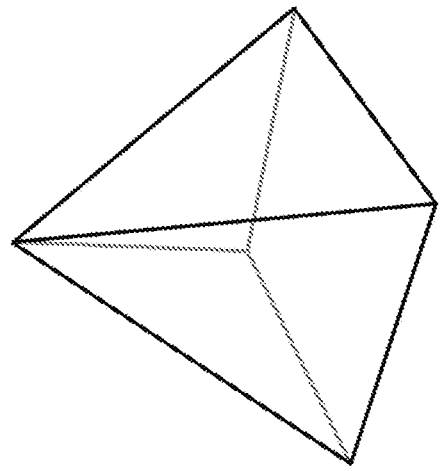
Figure 4D:
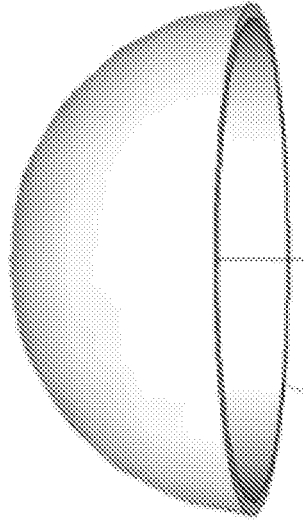

The at least one additional surface 124 can comprise any configuration, such as one or more side walls and a top wall. In one embodiment, as shown in FIG. 3, the side walls can be arranged at 90 degree angles with respect to one another, such that a box shape is formed in conjunction with the bottom surface 122. In another embodiment, the at least one additional surface 124 forms a curved side wall, such that a cylinder, elliptic cylinder, or cone is formed, as shown in FIGS. 4A-C. In another example arrangement, the at least one additional surface can form a dome-like shape over the bottom surface, as shown in FIG. 4D. In yet other embodiments, the side walls can form a triangular shape, as shown in FIG. 4E. It is to be understood that the above example configurations are non-limiting and that the at least one additional surface can have other configurations not provided in the aforementioned example configurations.

In another embodiment, the at least one additional surface 124 includes a second material that is gas permeable in order to effectuate the gas exchange that is to occur within the cell culture chamber. By fabricating the cell culture chamber such that the bottom surface is made of a material to which cells adhere, such as polystyrene, and the at least one additional surface, such as the side walls and/or the top wall, is made, at least in part, of a gas permeable material, high surface area-gas exchange is achieved in the systems of embodiments of the present invention. Having large surfaces with high permeability, other than the bottom surface, offers the ability to achieve greater levels of gas exchange without having to sacrifice the adherent nature of the bottom surface relative to prior art culture systems, which were limited in the amount of culture medium that could be included and/or lacked a culture-friendly surface to which cells can adhere.

In certain embodiments, the second material includes one or more materials having permeability to oxygen at or greater than a permeability coefficient of 350 and permeability to carbon dioxide at or greater than permeability coefficient of 2000 where the unit of permeability coefficient is $[cm^3][cm]/[cm^2][s][cm\ Hg]$. Example materials include silicone-containing materials such as poly(dimethyl siloxane) (PDMS), which is well known for high oxygen and carbon dioxide permeability (up to three orders of magnitude higher than materials such as polystyrene and PMMA), and polymethylpentene. In one example embodiment, the cell culture chambers comprise polystyrene floors and silicone side and top walls.

In certain aspects, in addition to the second material, the at least one additional surface 124 can also comprise the first material. For example, and not limitation, the additional surface 124, such as the one or more side walls and/or top wall, can incorporate the second material (e.g., a high permeability polymer, such as a silicone) within a frame made of the first material (e.g., polystyrene), as shown in FIG. 5. It is also contemplated that the bottom surface can also comprise the second material. However, in some embodiments, the second material is only be intermittently dispersed throughout the bottom surface to ensure that the first material covers a sufficient surface area such that cells can adhere to the surface.

The first material and the second material can be joined together using any methods known in the art, such as mechanical fastening, adhesive and solvent bonding, and welding. However, given that the cellular immunotherapeutic product produced using systems and methods of embodiments of the invention will be administered to a human patient, regulatory issues may prevent the use of certain, or all, adhesives in assembling the cell culture chambers. Accordingly, in certain embodiments, the first and second materials are joined without using adhesive. In one embodiment, all surfaces of the cell culture chamber, such as the bottom, side, and top walls, comprise the first material (e.g., polystyrene) and are joined together using ultrasonic welding, with at least a portion of the first material in the side and/or top walls cut out to allow for the insertion of a second material (e.g., a silicone material), as shown in FIG. 5. It is to be understood that the holes can be any shape desired, and not just the circles as shown in FIG. 5. In an example arrangement, the second material can be separately inserted into the holes in the same manner as a stopper that is inserted into the top opening of a vessel for sealing of the vessel. In another example, the second material can be fabricated to fully encompass and surround the outer surface of the first material frame, such that the second material is accessible through the holes within the frame, as shown in FIG. 5. It is to be understood that the aforementioned configurations are only examples and that other configurations for joining the first and second materials are also contemplated embodiments of the present invention.

The height of the one or more cell culture chambers can vary. For example, and not limitation, an example range of cell culture chamber heights includes heights of anywhere from 0.5 mm to 100 mm, such as 0.5, 1.0, 2.0, 3.0, 4.0, 5.0, 6.0, 7.0, 8.0, 9.0, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mm, or more, or any height therebetween. In certain embodiments, the heights of the chamber can be comparable to liquid heights in cultures that are typically performed in 6- and 24-well plates, such as between 2 and 6 mm, with a volume capacity of about 0.8 mL to 6 mL. In other embodiments, the cell culture chambers will be of large size, such as between 10 mm and 50 mm, with a culture surface of about 50 cm$^2$.

As briefly mentioned above with respect to FIG. 3, in certain embodiments, the bioreactors 110 will also include one or more pumps 140 operably coupled to the cell culture chamber 120 for perfusing perfusion medium into the cell culture chamber. The bioreactors 110 can also include one or more fluid reservoirs 132. The fluid reservoirs 132 are in fluidic communication with the cell culture chamber 110 and can be operably coupled to one or more pumps 140. One or more tubes for connecting the fluid reservoirs to the pumps and cell culture chamber are also provided. In certain aspects, the one or more pumps are configured for pumping fluid from the fluid reservoir, through the cell culture chamber, and into the waste collection reservoir. In the example embodiment shown in FIG. 3, fluid moves from the fluid reservoir 132, through tubing 152 to the pump 140 and into the cell culture chamber 120 via inlet 136, back out of the cell culture chamber 120 via outlet 138, through tubing 154, and into the waste collection reservoir 134.

In certain embodiments, the fluid reservoir and/or waste collection reservoir can each be provided as one or more capped bottles either contained within the cell culture chamber or fluidically coupled to the chamber. Each reservoir contains an inlet port and an outlet port, or an outlet port and a vent fluidically coupled to the inlet of one or more cell culture chambers. In certain aspects, for example, Luer connectors and silicone gaskets cut to fit around the Luer connectors can be used to prevent leakage through either or both of the inlet or outlet.

In certain embodiments, the one or more biological reactors are sized and configured to fit within an incubator, such that the process will be carried out within an incubator. Conditions within the incubator include sustained temperatures of 37° C. and 95-100% humidity. Thus, the materials chosen must have the integrity to withstand these conditions, given that the materials (including fluids and biologics) tend to expand under such conditions. Furthermore, in some circumstances, conditions within the incubator remain stable, and automated recording of the temperature is possible to have knowledge of temperature fluctuations to correlate with any aberrations in the reactions performed in the incubator. Accordingly, any supply of power should not change the environment within the incubator. For example, certain pumps generate heat. Accordingly, in one embodiment, the pumps are housed separately from the biological reactors, but are still in fluidic and operable communications with the reactors. In another embodiment, the pumps are directly attached to the biological reactors and located within the incubator, but are heat free or are operably connected to a heat sink and/or a fan to dissipate the heat. Regardless of the configuration, the pumps are operably coupled to the biological reactors, and, in turn, the cell culture chambers. Additional details regarding perfusion-based automated cell culture systems, such as small scale culture system for endothelial cell culture with on-board reagent storage and perfusion enabled by an on-board disposable peristaltic pump and a larger scale culture system for dendritic cell generation from monocytes using chambers with polystyrene bottom surfaces, can be found in International Patent Application Numbers PCT/US2016/040042 and PCT/US2016/60701, both of which are incorporated herein by reference in their entirety.

This system can also include a heater for controlling the temperature of the cell culture reservoir and optionally the fluid reservoir. In such a configuration, no incubator is required, and the system can operate autonomously, with only a source of electrical power. If the system lacks a heater, it can be operated inside of a cell culture incubator.

In still other aspects, the cell culture chamber includes one or more sensors (not shown) operably coupled to the cell culture chamber. The sensors may be capable of measuring one or more parameters within the cell culture chamber, such as pH, dissolved oxygen, total biomass, cell diameter, glucose concentration, lactate concentration, and cell metabolite concentration. In embodiments wherein the system includes multiple cell culture chambers, one or more sensors can be coupled to one or more of the cell culture chambers. In certain embodiments, one or more sensors are coupled to one or more cell culture chambers, but not all of the chambers in a system. In other embodiments, one or more sensors are coupled to all of the cell culture chambers in a system. In systems having multiple chambers operably coupled to one or more sensors, the sensors can be the same in each of the chambers to which they are coupled, they can all be different, or some sensors can be the same and some can be different. In certain aspects, the one or more sensors are operably coupled to a computer system (not shown in FIG. 3) having a central processing unit for carrying out instructions, such that automatic monitoring and adjustment of parameters is possible. Additional details regarding computer systems for implementing methods of the present invention using the cell culture chambers is provided below.

As also shown in FIG. 3, the cell culture chamber has an inlet 126 and an outlet 128, both of which can be used to fluidically couple the chamber via a fluidic connector with one or more additional vessels. In certain embodiments the additional vessels include one or more additional cell culture chambers, as will be described in more detail below. Systems of the present invention can include, for example, 2, 3, 4, 5, 6, 7, 8, 9, 10, 15, 20, 30, 40, 50, 60, 70, 80, 90, 100, or any number of cell culture chambers in between or higher than one hundred configured to fluidically connect with one another in a series to produce the immunotherapeutic product. Alternatively or additionally, one or more cell culture chambers can be arranged in parallel with one another to allow for production of immunotherapeutic product for more than one individual at a time. In a preferred embodiment, the cell culture chambers of the bioreactors are connected via a sterile connection.

Figure 6:
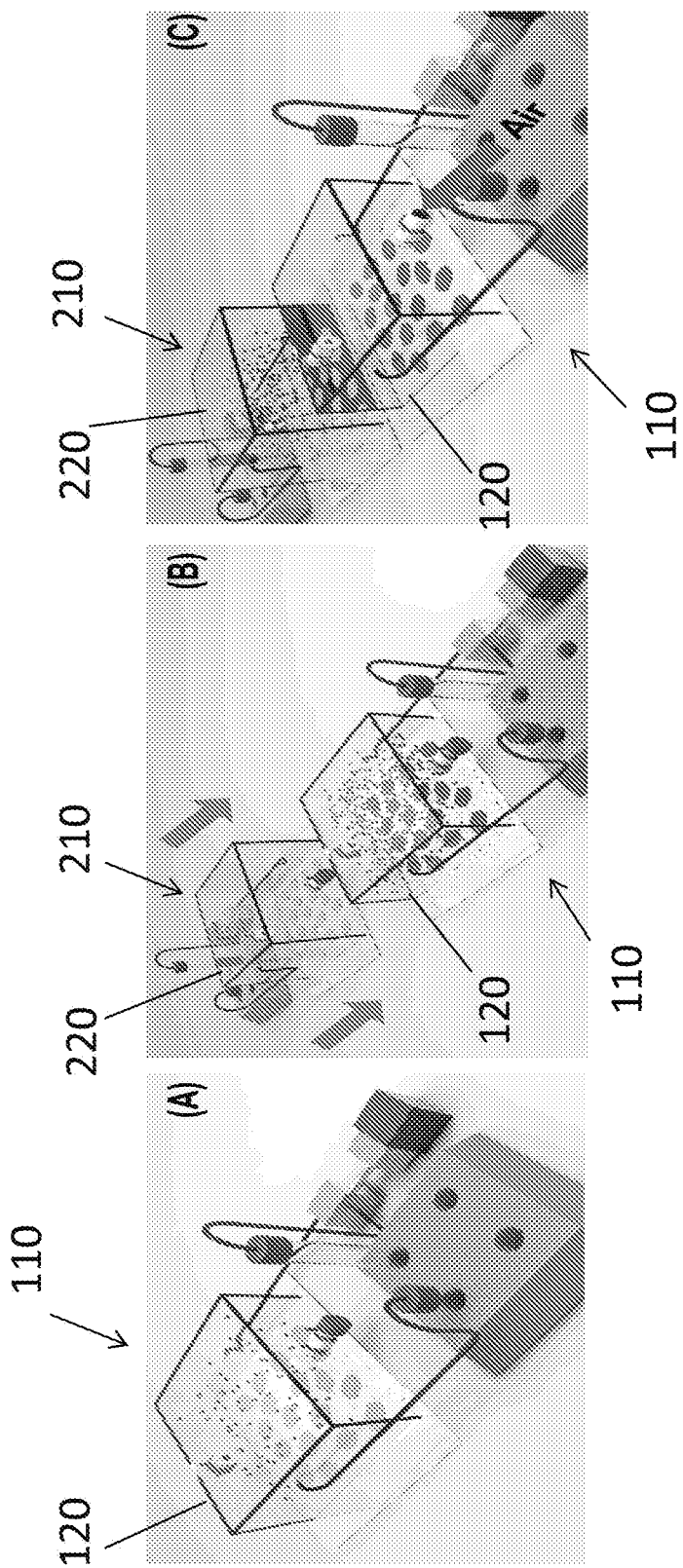
FIGS. 6A-C depict schematic representations of a process for connecting cell culture chambers and transferring fluid between them.

An example configuration of a multi-bioreactor system can be found in FIGS. 6B and C, with additional detail regarding the processes carried out using this configuration provided below. As shown in FIG. 6B, in the event that a second bioreactor 210 is involved, the second cell culture chamber 220 is moved into position to connect with the first cell culture 120 chamber via the outlet of the first chamber and the inlet of the second chamber. The connection is preferably a sterile connection. The connection allows for the injection of sterile air into the first cell culture chamber 120 to transfer the supernatant containing the expanded T-cells into the second cell culture chamber 220. Alternative techniques known in the art of fluid flow may be employed to transfer the supernatant from the first cell culture chamber 120 to the second cell culture chamber 220. As also shown, each bioreactor includes its own fluid and waste collection reservoirs, pumps, and associated tubing. However, it is to be understood that the reservoirs and pumps can be shared between bioreactors.

Figure 7:
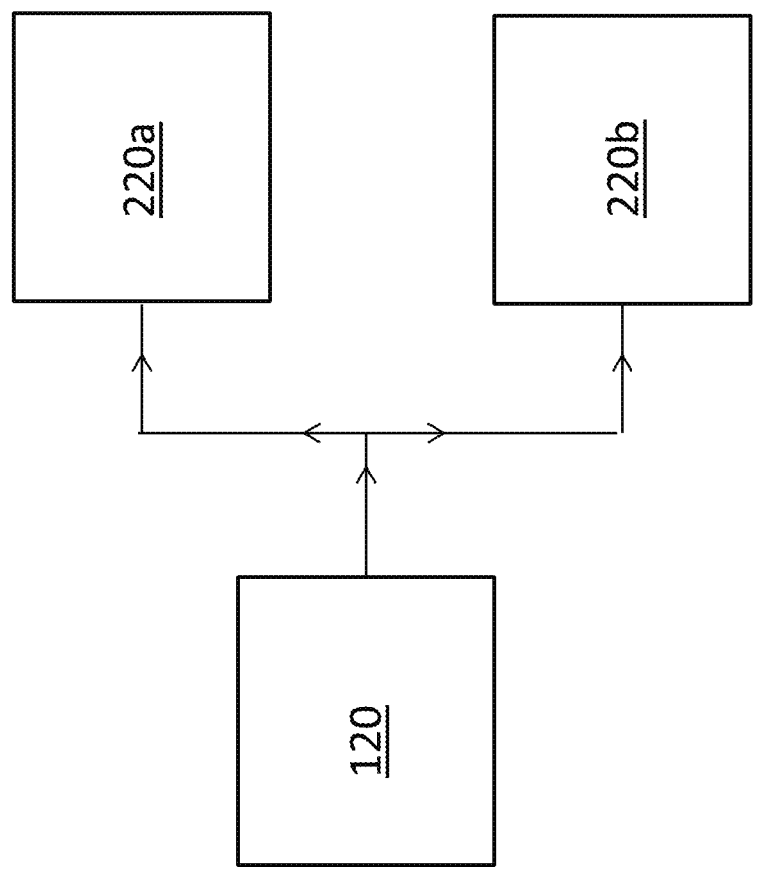
FIG. 7 depicts the flow of fluid from the outlet of one cell culture chamber to the inlets of two cell culture chambers in accordance with one embodiment.

In certain embodiments, there is a 1:1 ratio of cell culture inlets to cell culture outlets, such as when the one or more biological reactors are arranged in series with one another, as shown in FIGS. 6B and C. In other embodiments, the ratio of outlets to inlets for at least a portion of biological reactors is 1:2. For example, the outlet of one cell culture chamber 120 can be fluidically connected to the inlet of two cell culture chambers 220a and 220b, such that fluid flowing out of the first cell culture chamber 120 is split into two streams, sending one stream into a second cell culture chamber 220a and second stream into a third cell culture chamber 220b, as shown in FIG. 7. In this configuration, both the second 220a and the third 220b cell culture chambers can be used to further stimulate and expand the T-cells. Additionally, or alternatively, one of the second 220a or third 220b cell culture chambers can be configured to allow for the monitoring of reaction and flow parameters using one or more sensors operably coupled to the chamber. In this way, one of the chambers remains free from additional sensors, some of which may need to penetrate the walls of the cell culture chamber, which can add to the risk of leakage and/or contamination.

In certain embodiments, the one or more biological reactors can be provided in a system containing modules for effectuating various other processes prior to, concurrent with, or subsequent to the process occurring within the cell culture chambers of the biological reactors.

The system and some or all of its components can be designed using CAD software and then transferred to a laser cutter, which allows the plastic to be cut to the specified size and shape. The various connections, such as inlets and outlets, can be made by laser cutting through holes which can then be then tapped manually to provide threads for accepting male Luer fittings. Fluid can later be introduced to the system by connecting the Luer adapter to a blunt dispensing needle with tubing pushed onto the blunt needle portion. Additional detail regarding construction of fluidic system components can be found in International Patent Application Numbers PCT/US2016/040042 and PCT/US2016/60701, both of which are incorporated herein by reference in their entirety.

The above description focuses on the system components and various possible configurations. The following description focuses on the processes that are carried out using example embodiment systems of the invention. In order to stimulate and expand antigen-specific T-cells, the process begins with a co-culture of T-cell containing cells with APCs obtained from the same individual in a cell culture chamber. In a particular embodiment, the T-cell containing cells include peripheral blood mononuclear cells (PBMCs) and the APCs include DCs. The T-cell containing cells and APCs can be provided to the cell culture chamber in a ratio (T-cell containing cells:APCs) from about 1000:1 to 1:1000 of about, such as, for example and not limitation, 1000:1, 900:1, 800:1, 700:1, 600:1, 500:1, 400:1, 300:1, 200:1, 100:1, 75:1, 50:1, 25:1, 20:1, 15:1, 10:1, 5:1, 4:1, 3:1, 2:1, 1:1, 1:2, 1:3, 1:4, 1:5, 1:6, 1:7, 1:8, 1:9, 1:10, 1:15, 1:20, 1:50, 1:75; 1:100, 1:200: 1:300, 1:400, 1:500, 1:600, 1:700, 1:800, 1:900, 1:1000, or any ratio therebetween. In one aspect, a ratio of 10:1 is preferred.

In order to initiate stimulation and expansion of T-cells from the interaction of APCs with T-cell containing cells, the APCs need to be stimulated. This can be done through the use of one or more stimulatory molecules. In certain embodiments, the stimulatory molecule is non-tumor specific. In other embodiments, the stimulatory molecule is tumor specific. For example, the stimulatory molecule can be chosen from one or more characteristics of an individual's tumor, such as different antigen peptides. In some embodiments, the stimulatory molecule is preferably added only in the beginning of a culturing cycle. The stimulatory molecule can be added over a period of only about a few minutes, an hour, a few hours, or longer. In one preferred embodiment, the stimulatory molecules are added over about an hour time period.

During culturing of the two cell materials, a supernatant is formed containing lighter non-adherent T-cells, whereas the heavier, mature APCs (e.g., dendritic cells) adhere to the bottom surface. In those embodiments wherein DCs are used as the APCs, the expanded T-cells must be extracted from the cell culture chamber by the end of the seven days because primary DCs cannot be maintained for more than seven days in culture. Thus, if additional expansion of T-cells is desired, a fresh supply of dendritic cells is needed. It is also to be understood that the culturing of cells using one batch of dendritic cells can be for any period of time less than seven days. For example, the cells can be cultured for a period of anywhere from less than a minute to seven days, with the duration of culture dependent on the extent of stimulation desired.

In an example embodiment, after up to seven days in culture, the expanded T-cells are extracted and transferred to a new cell culture chamber containing fresh DCs pulsed with, for example, the same antigen peptides used in the first cell culture chamber. The stimulation process can be repeated as many times as needed in order to generate a sufficiently large number of cells for a therapeutic dose of T cells. When using a culture surface area comparable to that of typical well plates, the stimulation process is typically repeated four times to generate a sufficient supply of T-cells.

The co-culturing of APCs and T-cells takes place in a culture medium. Example culture media include, but are not limited to, RPMI medium, and Cellgenix® medium. Any other suitable culture medium known in the art can be used in accordance with embodiments of the present invention. Cytokines such as IL-4 and GM-CSF can also be added to the culture medium.

In one embodiment, a perfusion of medium and cytokines can be provided to the cellular mixture within the cell culture chamber(s) to assist with the formation of the cell-based immunotherapeutic product. In plate-based protocols for stimulation of T cells by DCs, a culture volume of approximately 2 mL is maintained from the start, with infusion of cytokines occurring twice within each 7 day stimulation period. A major advantage of perfusion is the ability to maintain consistent local concentration profile of medium and cytokines, which ensures greater yields and the potential ability to speed up the process of monocyte differentiation to DCs compared to prior art plate-based protocols. However, the combination of adherent (DC) and non-adherent (T cell) types, along with the high sensitivity of DCs to mechanical forces poses challenges to the stimulation and expansion of antigen-specific T-cells, especially with respect to the flow of fluid through the cell culture chamber. Thus, in those embodiments in which medium and cytokines are provided via perfusion, systems of the present invention must be able to supply cells with nutrients and cytokines without removing cells from the bioreactor while also taking into account the shear sensitivity of certain antigen-presenting cells, such as DCs. Essentially, some embodiment systems and methods of the invention aim to optimize retention of autocrine/paracrine signals favoring T cell proliferation while refreshing growth factors and maintaining minimal physical stimulation of DCs. In order to account for this, both the direction and the rate of perfusion flow through the cell culture chamber must be taken into consideration.

In certain aspects, the fluid flow rate is maintained below the sedimentation rate of the antigen-presenting cells. As such, the antigen-presenting cells will remain within the culture chamber because of their mass. In other words, the antigen-presenting cells will sink toward the bottom of the cell culture chamber and therefore remain in the cell culture chamber.

A flow rate that is lower than the sedimentation rate can be calculated according to Equation 1:

$$v\_max = [(\psi d\_p)]^2 / 150\mu \; g(\rho\_cell - \rho\_liquid)\varepsilon^3(1-\varepsilon)$$

where v_max is the liquid velocity beyond which cells will be lifted upwards, ψ is shape factor of cells (ratio of surface area of the cells to surface area of a sphere of equal volume; note that cells are not perfectly spherical and this factor is expected to be below 1), d_p is a diameter of a spherical particle of volume equal to that of a cell, μ is viscosity of liquid containing cells, g is the gravitational constant ρ_cell is the density of cells, ρ_liquid is a density of liquid containing cells, and ε is a fraction of the volume of interest that is not occupied by cells.

Figure 8:
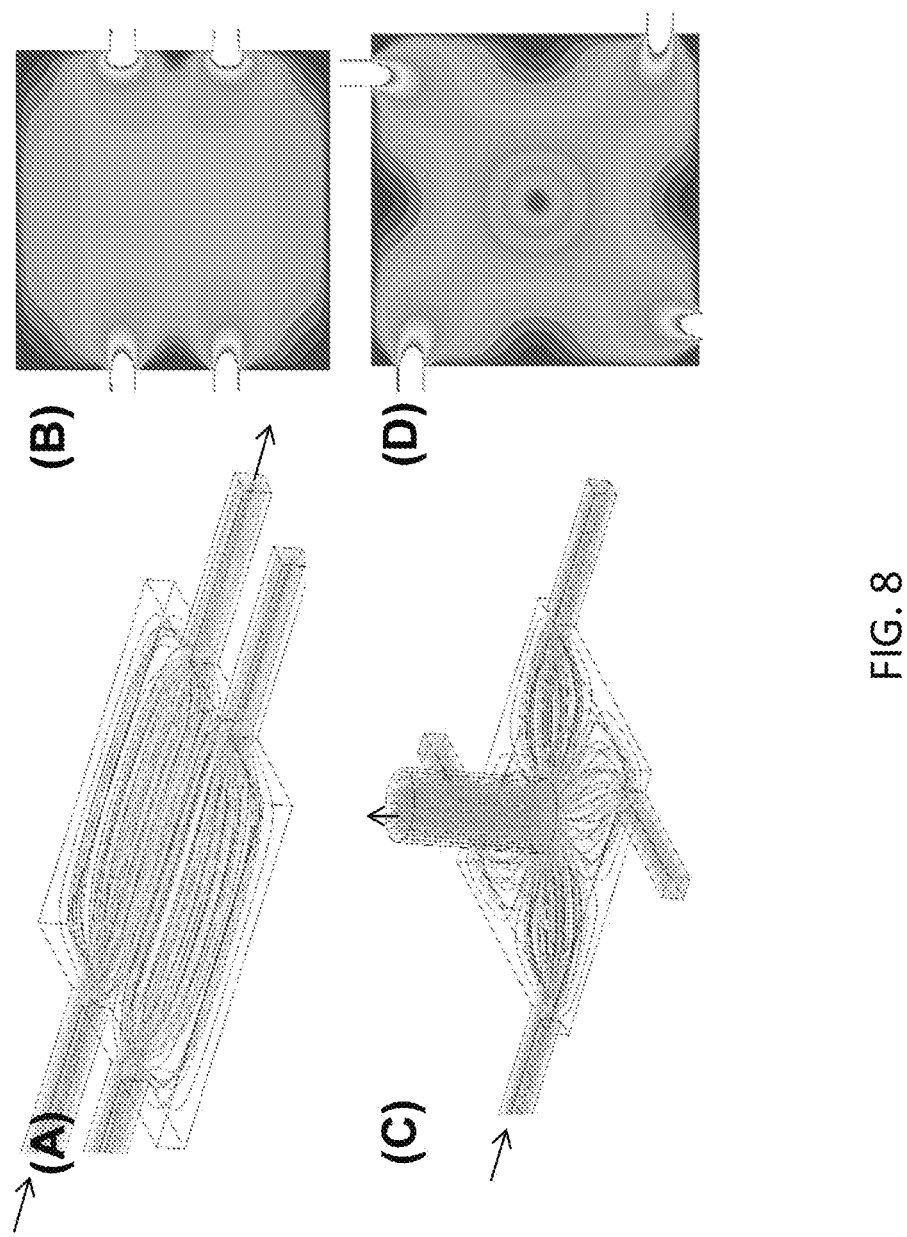
FIGS. 8A-D depict the flow of fluid through various chamber configurations.

In other aspects, the one or more inlets 136 and the one or more outlets 138 of the cell culture chamber are arranged to move fluid, such as perfusion fluid, within the cell culture chamber along a vertical flow path. This configuration helps to prevent cells (e.g., both DCs and T-cells) from leaving the chamber, especially when flow rates through the chamber are in the range of 2-10 L/min. For example, a planar in/out flow, as shown in FIGS. 8A and B, provides regions of high wall shear uniformity but requires measures to prevent removal of cells from the chamber. By contrast, a configuration with symmetric inflows and vertical outflow, as shown in FIGS. 8C and D, can prevent cells from leaving the chamber.

Although shown in FIG. 8C as having four inlets and one vertical outlet, any number of inlets and outlets can be provided, as long as the fluid flowing out of the chamber flows in the vertical direction out of the top of the chamber. For example, the chamber can have any one of 1, 2, 3, 4, 5, 6, 7, 8, 9, 10, or more perfusion fluid inlets, while also having any one of 1, 2, 3, 4, 5, 6, 7, 8, 9, 10, or more perfusion fluid outlets. Additionally, while the inlets are shown as symmetrical in FIG. 8C, it is also contemplated that configurations containing two or more inlets are not arranged symmetrically. The inlet can also direct fluid to enter the chamber from any direction. In a preferred embodiment, the inlet directs fluid to enter the chamber in a direction that is parallel to the bottom surface.

In certain aspects, medium perfusion occurs at specific points in time over the time period in which the cells are cultured in any one cell culture chamber, such as, for example, 1, 2, 3, 4, 5, 6, 7, 8, 9, 10, or more times each day or week. In other aspects, medium is continuously perfused during culturing. Continuous perfusion helps to maintain a near constant culture volume throughout the process.

In certain aspects, cytokines are infused at one or more points during culturing, such as, for example, 1, 2, 3, 4, 5, 6, 7, 8, 9, 10, or more times. Alternatively, cytokines can be continuously perfused with medium. In those embodiments, the continuous perfusion helps maintain a consistent local concentration profile of cytokines, which can help to ensure greater yields and has the ability to increase the speed at which T-cells are stimulated and expanded compared to static cell culture methods.

Perfusion parameters can be varied at any time during a culture cycle. Example parameters include, but are not limited to, the median flow rate, cytokine concentration, and duration of culture cycle. Each of these parameters may have an impact on the efficacy of T-stimulation. For example, in recent work designing culture chambers for monocyte-diffusion to DCs, as described in International Patent Application Nos. PCT/US2016/040042 and PCT/US2016/60701, we have determined that medium perfusion rates corresponding to wall shear stress levels of 0.1 dyn/cm2 are capable of producing DCs that are phenotypically identical to those generated using conventional 6- or 24-well plate-based protocols. As such, by measuring the one or more of the phenotypic and functional measures described above during the culture cycle, the effect of one or more perfusion parameters on efficacy can be monitored, allowing for appropriate adjustments.

In accordance with certain aspects, the stimulation efficacy can be assessed at any point during the culturing, preferably after seven days. Both phenotypic and functional measures can be used to assess the efficacy. For example, cell number (fold-expansion) can be calculated using directed cell counting methods. Cell phenotype, including assessment of antigen-specificity by tetramer staining, can be characterized by flow cytometry. Functional assays can also be used to assess the ability of expanded T cells to recognize antigen-loaded target cells as well as autologous tumor cell. The results can be benchmarked against DC-based T cell stimulations carried out in both 24-well plate and G-Rex® formats.

As described above, because certain APCs, such as dendritic cells, cannot survive in culture beyond seven days, certain embodiments of the present invention involve multiple cycles of T-cell stimulation using more than one bioreactor in semi-batch configurations. Each cycle is performed with freshly generated autologous antigen-presenting cells. In certain embodiments, the antigen-presenting cells are pulsed with the same set of antigens for each stimulation cycle. In other embodiments, different sets of antigens are used for one or more of the stimulation cycles.

In general, multiple cycle T-cell stimulation involves the culturing of cells in a first cell culture chamber in a manner that generates a supernatant comprising a first cell product, the provision of a second cell culture chamber, and the subsequent transfer of supernatant from the first cell culture chamber to the second cell culture chamber by introducing a gas flow into the first cell culture chamber, as shown in FIG. 2.

An example configuration of a multi-reactor system can be found in FIGS. 6A-6B. As shown, the process begins with one reactor containing mature, adhered DCs, which will be loaded with PBMCs and subjected to an initial stimulation cycle of 7 days with perfusion of medium and cytokines. Following the end of the first stimulation cycle, a second, optionally larger, reactor containing fresh DCs will be connected to the first reactor, as illustrated in FIGS. 6B and 6C. An injection of sterile air will then transfer the supernatant from the first reactor to the second reactor. This second bioreactor will contain its own supply of medium and cytokines in on-board containers along with a disposable peristaltic pump. Following the transfer of supernatant, the first reactor can be uncoupled and discarded. This process can be repeated for as many times as desired with progressively larger bioreactors to achieve the desired level of stimulation and T cell proliferation. For example, in one embodiment, four cycles of stimulation are carried out involving the transfer of supernatant to a new cell culture chamber three different times. It is to be understood that although the second chamber 220 is shown as being larger than the first cell culture chamber 110, the second, and any subsequent cell culture chamber, can be any size, such as larger than, the same size as, or smaller than the first cell culture chamber. In certain embodiments, each subsequent cell culture chamber is larger in size than the preceding cell culture chamber from which the supernatant is being transferred.

The modularized design provides flexibility both in terms of number of cycles as well as type of antigen-presenting cells, which can either be prepared using the same set of antigens for each cycle, a different set of antigens for each cycle, or a combination of the former and latter. In certain aspects, the ability to produce T-cells specific for multiple different antigens associated with the disease in one automated process is advantageous in the treatment of the disease, as it allows for a multi-prong attack.

In certain aspects, computational modeling approaches are used to optimize the interaction of T-cells with antigen-presenting cells such as DCs. Computational models in accordance with the present invention take into account the impacts of perfusion and the optimal time required for stimulation, and incorporate both particle interaction-based as well as kinetic parameter-based approaches. Example particle interaction-based and kinetic parameter-based approaches are known in the art, some of which are described herein. For example, with respect to particle interaction-based approaches, Day and Lythe describe the time required for a T cell to find an APC on the surface of a lymph node using the following expression, where D is the diffusivity of the T cell, and b is the radius of the APC located centrally within a spherical lymph node of radius R. See Day et al., Mathematical Models and Immune Cell Biology; 2011

$$\tau' = \frac{1}{\frac{4}{3}\pi(R^3 - b^3)4} \int_b^R 4\pi r^2 F(r) dr = \frac{R^3}{3Db} - \frac{3}{5}\frac{R^2}{D} + \frac{2}{3}\frac{b^2}{D} + \cdots$$

Figure 9:
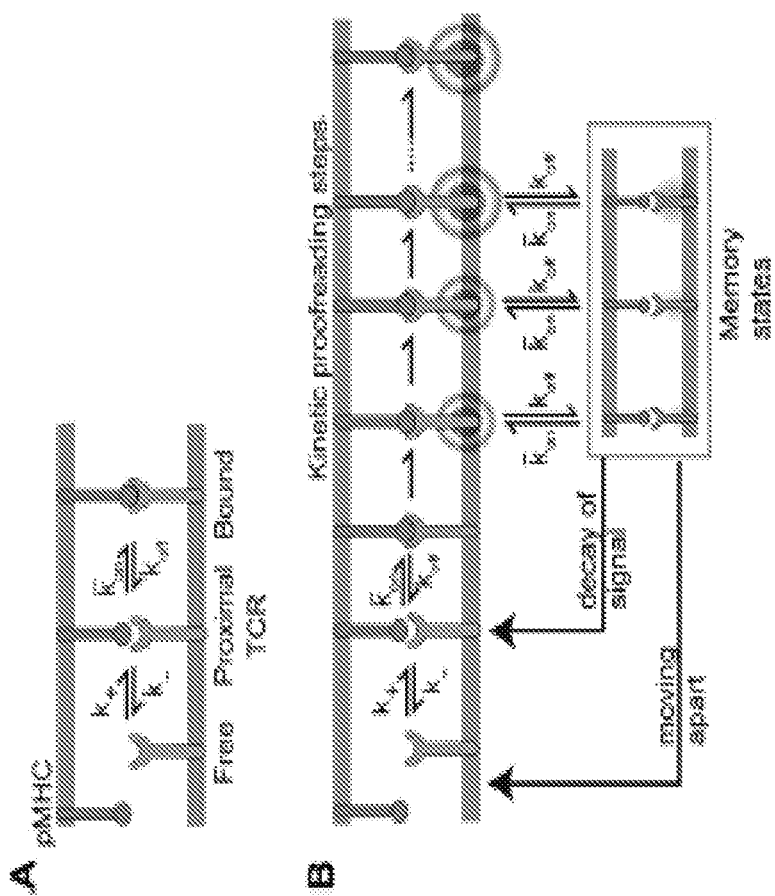
FIG. 9 depicts kinetic parameter-based modeling of interactions between T cells and antigen-presenting cells.

With respect to kinetic parameter-based approaches, Valitutti has developed a model of the interactions between T-cells and antigen-presenting cells, as shown in FIG. 9.

Valitutti et al., FEBS Lett. 2010. However, such interactions have not been modeled within the context of a culture chamber or bioreactor.

By incorporating both particle interaction-based as well as kinetic parameter-based approaches into the computational models of the present invention, automated determination and monitoring of the optimal perfusion rate of a perfusion fluid (e.g., cytokine infused medium) for maximizing the probability of two cell types contacting each other within the cell culture chamber can be achieved.

For example, in certain embodiments, a cell culture system is provided that includes a cell culture chamber and a central processing unit comprising memory containing instructions executable by the central processing unit. In certain aspects, the instructions cause the system to receive as a first input data comprising a size of the cell culture chamber, receive as a second input data comprising a first concentration of a first cell type and a second concentration of a second cell type in one or more fluids that will be introduced into the cell culture chamber, and calculate, based on the first and second inputs, a perfusion rate of a perfusion fluid that will be introduced into the cell culture chamber that maximizes a probability of the first cell type and the second cell type contacting each other within the cell culture chamber. Additional details regarding computer systems for implementing the methods of the present invention within cell culture systems are provided below.

In some aspects, the system also includes one or more pumps operably coupled to one or more perfusion fluid reservoirs and operably coupled to the central processing unit, such that the central processing unit also controls the perfusion rate of the perfusion fluid by controlling the one or more pumps.

As described above, systems and methods of the invention utilize modules (e.g., bioreactors containing cell culture chambers, etc.) that are fluidically coupled to one another for processing an individual's cellular material to produce an immunotherapeutic product.

Systems, or devices, of the invention are modular and capable of fluidic connection to other similar devices in series (i.e., with fluid flowing from one device into another) and/or in parallel, and may also be so configured as to physically stack with one another or be capable of physical arrangement within a related device such as an incubator. The modular design of the system specifically allows for modules to be flexibly switched in and out depending on a desired process to be included within the system.

Fluidic devices of the invention, including the biological reactors comprising cell culture chambers, can be provided in either a microfluidic embodiment (i.e., wherein one or more channels or chambers therein has a dimension in the range of from about 1 µm to about 999 µm) or a macrofluidic embodiment (wherein all of the channels or chambers therein have dimensions of about 1 mm or more), or both.

The fluidic devices can further include additional fluid channels or compartments, gaskets or seals, mixing zones, valves, pumps, vents, channels for pressurized gas, electrical conductors, reagents, ports, and tubing as required by a particular design. They also may contain one or more control modules, transmitters, receivers, processors, memory chips, batteries, displays, buttons, controls, motors, pneumatic actuators, antennas, electrical connectors, and the like. The devices preferably contain only materials that are nontoxic to mammalian cells and that are compatible with sterilization by the use of alcohol and/or heat or other means, such as exposure to gamma radiation or ethylene oxide gas.

The materials of equipment are chosen with the appropriate chemical compatibility under different temperature and pressure rating specific to each process. Additionally, the choice of pumps implemented in the device, such as syringe, peristaltic, pressure, and rotary pump, ranges from a nL to a mL in flow rates and 10 to 10,000 psi in pressure depending on the flow and pressure requirements for the different functions.

Systems of the invention can also include one or more sample solution reservoirs or well or other apparatus for introducing a sample to the device, at various inlets of the modules, which are in fluid communication with an inlet channel. Reservoirs and wells used for loading one or more samples onto the fluidic device of the present invention includes but are not limited to, syringes, cartridges, vials, eppendorf tubes and cell culture materials (e.g., 96 well plates).

Where useful, surfaces of the devices can be made more hydrophilic, such as by exposure to a plasma, or can be coated with one or more gels, chemical functionalization coatings, proteins, antibodies, proteoglycans, glycosaminoglycans, cytokines, or cells. Fluidic devices of the invention are preferably devoid of fluid leaks under operating conditions and capable of sterile operation over a period of days to weeks. Fluidic devices of the invention also include a sampling mechanism that allows fluid to be removed from the system for testing without introducing new material or contaminants to the system.

In certain aspects, at least part of the cell culture system comprises disposable components, some or all of which can be housed within a non-disposable frame. In other aspects, all components of the system are disposable. Furthermore, in some embodiments, the cell culture system includes a sample tracking component for tracking and documenting patient material.

At least one step, and sometimes a plurality or all steps, during the manufacturing process are monitored for product characteristics (e.g., purity and polymorphic forms) using a variety of inline process analytical tools (PAT) or miniaturized micro-total analysis system (micro-TAS).

As described above, the cell culture systems of the present invention are capable of controlling the direction and flow of fluids and entities within the system. Systems of the invention can use pressure drive flow control, e.g., utilizing valves and pumps, to manipulate the flow of cells, reagents, etc. in one or more directions and/or into one or more channels of a fluidic device. However, other methods may also be used, alone or in combination with pumps and valves, such as electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No. 5,656,155).

Systems of the invention can also include or be operably coupled to one or more control systems for controlling the movement of fluid through the system; monitoring and controlling various parameters, such as temperature, within the systems; as well as detecting the presence of cell-based immunotherapeutic products, quantity of product (directly or indirectly), conversion rate, etc. The system may also be equipped with numerous classes of software, such as an advanced real-time process monitoring and control process, allowing for feedback control, as well as processes that allow integration and scale-up given reaction and purification results obtained using the system.

In certain embodiments, the system includes a combination of micro-, or macro-fluidic modules and tubing that are interchangeable in terms of channel dimensions, flow geometry, and inter-connections between the different modules of the device. Each module and tubing may be designed for a specific function. In one embodiment, all of the modules within the system are designed for cell culturing and T-cell stimulation. In other embodiments, the modules with the system are designed for different functions, such as tissue processing, dendritic cell generation, cell culturing, concentration, and/or purification, all integrated for the continuous manufacturing of an immunotherapeutic product. Both homogenous and heterogeneous processes are considered which are suitable for flow application. These processes are designed and optimized with respect to the starting materials and operating conditions, such as temperature, pressure and flow rates so as to not readily clog the system during the flow process.

The method of device scale-up is performed by parallel addition of module reactors or enlargement of the module channels while maintaining a set of dimensionless parameters characteristic to each process constant and dimensional parameters within the upper and lower bound limit. During process integration and optimization, the process decision variables, including temperature, pressure, flow-rate and channel dimensions, are varied to achieve the desired trade-off between yield, purity and throughput. Throughout the optimization process, the aforementioned set of dimensionless parameters undergoes an algebraic optimization with operational constraints. The operational constraints are the lower and upper bound of the decision variables. The objective function considers a combination of purity, yield and throughput operating variables. While the dimensionless parameters determine the steady-state quality of the device, the start-up quality of the device is also useful as it determines the time required to reach steady state and, in turn, the productivity of the device in the form of lag-time and waste. The start-up dynamics are analyzed using both simulation and experimentation, the results of which are used to perform a start-up optimization by implementation of real-time feedback control.

Aspects of the present disclosure described herein, such as control of the movement of fluid through the system, as described above, and the monitoring and controlling of various parameters, can be performed using any type of computing device, such as a computer or programmable logic controller (PLC), that includes a processor, e.g., a central processing unit, or any combination of computing devices where each device performs at least part of the process or method. In some embodiments, systems and methods described herein may be performed with a handheld device, e.g., a smart tablet, a smart phone, or a specialty device produced for the system.

Methods of the present disclosure can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer program include, by way of example, both general and special purpose microprocessors, and any one or more processor of any kind of digital computer. Generally, a processor will receive instructions and data from a read-only memory or a random access memory or both. Elements of computer are a processor for executing instructions and one or more memory devices for storing instructions and data. Generally, a computer will also include, or be operatively coupled to receive data from or transfer data to, or both, one or more non-transitory mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through network by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to embodiments of the invention involves transforming a tangible, non-transitory, computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification tags or chips, or any other medium which can be used to store the desired information and which can be accessed by a computing device.

As one skilled in the art would recognize as necessary or best-suited for performance of the methods of the invention, a computer system or machines employed in embodiments of the invention may include one or more processors (e.g., a central processing unit (CPU) a graphics processing unit (GPU) or both), a main memory and a static memory, which communicate with each other via a bus.

Figure 10:
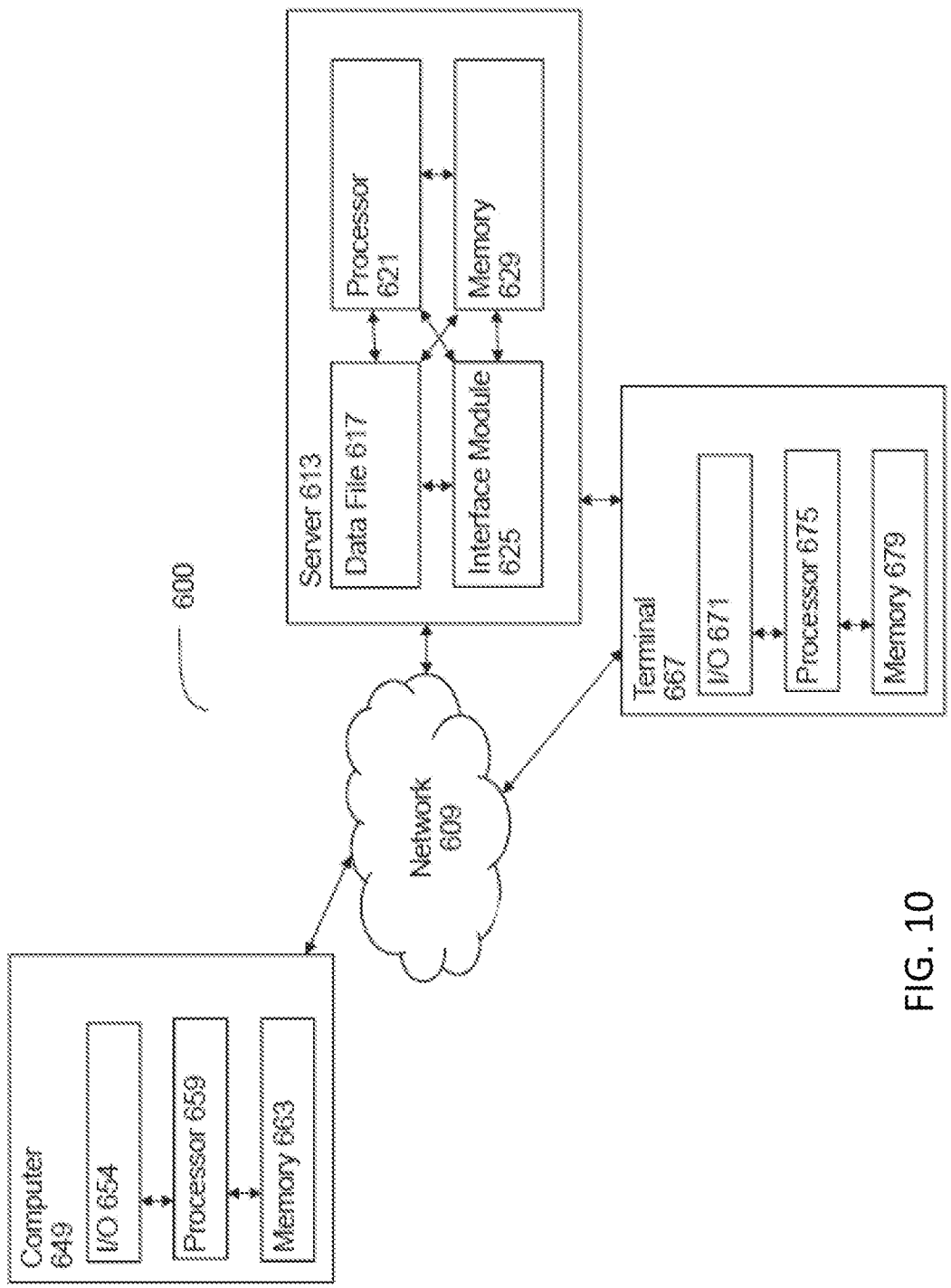
FIG. 10 depicts a system of the invention in accordance with certain embodiments.

In an example embodiment shown in FIG. 10, system 600 can include a computer 649 (e.g., laptop, desktop, or tablet). The computer 649 may be configured to communicate across a network 609. Computer 649 includes one or more processor 659 and memory 663 as well as an input/output mechanism 654. Where methods of the invention employ a client/server architecture, operations of methods of the invention may be performed using server 613, which includes one or more of processor 621 and memory 629, capable of obtaining data, instructions, etc., or providing results via interface module 625 or providing results as a file 617. Server 613 may be engaged over network 609 through computer 649 or terminal 667, or server 613 may be directly connected to terminal 667, including one or more processor 675 and memory 679, as well as input/output mechanism 671.

System 600 or machines according to example embodiments of the invention may further include, for any of I/O 649, 637, or 671 a video display unit (e.g., a liquid crystal display (LCD) or a cathode ray tube (CRT)). Computer systems or machines according to some embodiments can also include an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Memory 663, 679, or 629 according to example embodiments of the invention can include a machine-readable medium on which is stored one or more sets of instructions (e.g., software) embodying any one or more of the methodologies or functions described herein. The software may also reside, completely or at least partially, within the main memory and/or within the processor during execution thereof by the computer system, the main memory and the processor also constituting machine-readable media. The software may further be transmitted or received over a network via the network interface device.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

While the present invention has been described in conjunction with certain embodiments, one of ordinary skill, after reading the foregoing specification, will be able to effect various changes, substitutions of equivalents, and other alterations to the compositions and methods set forth herein.

The invention claimed is:

1. A cell culture chamber for co-culturing adherent and non-adherent cells, the cell culture chamber comprising:
   a bottom surface comprised of a first material to which antigen-presenting cells adhere;
   at least one additional surface, wherein the at least one additional surface is comprised of a second material that is gas permeable, wherein the second material comprises one or more materials having a permeability to oxygen at or greater than a permeability coefficient of 350 $[cm^3][cm]/[cm^2][s][cm\ Hg]$ and a permeability to carbon dioxide at or greater than a permeability coefficient of 2000 $[cm^3][cm]/[cm^2][s][cm\ Hg]$, wherein the second material is incorporated within a frame of the first material in one or more of a perimeter of one or more side walls, a top surface, and the bottom surface of the cell culture chamber;
   at least four inlets arranged horizontally relative to the bottom surface and symmetrically to each other in the perimeter of the one or more side walls, wherein a position of the at least four inlets directs one or more fluids to enter the cell culture chamber as symmetric inflows substantially parallel to the bottom surface; and one or more outlets arranged to direct one or more fluids from the cell culture chamber as a substantially vertical outflow relative to the bottom surface, wherein the position of the at least four inlets in the perimeter of the one or more side walls of the cell culture chamber, together with a position of the at least one outlet at the center in the top surface of the cell culture chamber provide a symmetric inflow and a vertical outflow to minimize a shear force of the one or more fluids acting on the antigen-presenting cells and the non-adherent cells co-cultured in the cell culture chamber to retain the co-cultured cells within the cell culture chamber.

2. The cell culture chamber of claim 1, wherein the bottom surface and the at least one additional surface are joined together without using an adhesive.

3. The cell culture chamber of claim 1, wherein the first material comprises polystyrene.

4. The cell culture chamber of claim 1, wherein the second material comprises one or more materials selected from of the group consisting of: silicone and polymethylpentene.

5. The cell culture chamber of claim 1, wherein the at least one additional surface further comprises the first material.

6. The cell culture chamber of claim 1, further comprising at least one fluidic connector configured to fluidically couple the cell culture chamber to a second vessel.

7. The cell culture chamber of claim 6, wherein the second vessel is a second cell culture chamber.

8. The cell culture chamber of claim 1, further comprising one or more pumps fluidically coupled to the one or more inlets and one or more outlets.

9. The cell culture chamber of claim 8, further comprising one or more fluid reservoirs operably coupled to the one or more pumps.

10. The cell culture chamber of claim 9, further comprising one or more sensors operably coupled to the cell culture chamber in a manner that the one or more sensors are able to measure one or more parameters within the cell culture chamber.

11. The cell culture chamber of claim 10, wherein the one or more parameters are selected from the group consisting of: pH, dissolved oxygen, total biomass, cell diameter, glucose concentration, lactate concentration, and cell metabolite concentration.

12. The cell culture chamber of claim 10 further comprising a central processing unit communicatively coupled to the one or more sensors and configured to adjust an operating state of the one or more pumps as a function of the one or more parameters measured.

13. The cell culture chamber of claim 9, wherein the cell culture chamber is sized and configured to fit within an incubator.

14. The cell culture chamber of claim 13, wherein the one or more pumps are within the incubator.

15. The cell culture chamber of claim 13, wherein the one or more pumps are outside of the incubator and operably coupled to the cell culture chamber within the incubator.

16. The cell culture chamber of claim 1, wherein movement of the one or more fluids as the vertical outflow is such that a fluid flow rate is insufficient to overcome a settling rate of cells within the cell culture chamber.

* * * * *